US009320484B2

(12) United States Patent
McKenna

(10) Patent No.: US 9,320,484 B2
(45) Date of Patent: Apr. 26, 2016

(54) VIBRATION DAMPING FOR APPARATUS COMPRISING ROTATING GANTRY

(75) Inventor: Gilbert W. McKenna, Revere, MA (US)

(73) Assignee: Analogic Corporation, Peabody, MA (US)

(*) Notice: Subject to any disclaimer, the term of this patent is extended or adjusted under 35 U.S.C. 154(b) by 62 days.

(21) Appl. No.: 14/130,001

(22) PCT Filed: Jun. 30, 2011

(86) PCT No.: PCT/US2011/042567
§ 371 (c)(1),
(2), (4) Date: Dec. 30, 2013

(87) PCT Pub. No.: WO2013/002800
PCT Pub. Date: Jan. 3, 2013

(65) Prior Publication Data
US 2014/0119515 A1    May 1, 2014

(51) Int. Cl.
H05G 1/02 (2006.01)
H02K 5/24 (2006.01)
(Continued)

(52) U.S. Cl.
CPC .......... A61B 6/4429 (2013.01); A61B 6/44 (2013.01); F16C 19/527 (2013.01); H02K 5/24 (2013.01);
(Continued)

(58) Field of Classification Search
CPC .......... A61B 6/00; A61B 6/44; A61B 6/4429; A61B 6/4439; H05G 1/00; H05G 1/02; H05G 1/04; F16C 19/00; F16C 19/22; F16C 19/24; F16C 19/26; F16C 19/30; F16C 19/305; F16C 19/50; F16C 19/502; F16C 19/505; F16C 19/507; F16C 19/527; F16C 19/54; F16C 19/541–19/543; F16C 19/545–19/548; F16C 27/00; F16C 27/04; F16C 27/06; F16C 27/066; F16C 27/08; F16C 33/00; F16C 33/30; F16C 33/34; F16C 33/46; F16C 33/46; F16F 15/14; F16F 15/1485; F16F 15/1492; F16F 15/20; F16F 15/10; F16F 15/1201; F16F 15/1207; F16F 15/1208; F16F 15/00; F27B 7/22; F27B 7/2206; F27B 7/2226; F27B 7/2246; F27B 7/2273; F27B 7/228; F27B 7/2286; H02K 5/00; H02K 5/02; H02K 5/04; H02K 5/16; H02K 5/173; H02K 5/24; B29L 2031/04; B29L 2031/32; B29L 2031/721
USPC ............... 378/4, 15, 167, 181, 189, 193, 197, 378/198, 204, 210; 384/416, 418, 419, 428, 384/439–442, 444, 548, 549, 551, 553, 558, 384/564, 565, 567, 568, 582, 576, 578, 581, 384/586, 587, 593, 597, 618–620, 627; 492/15, 16, 57–59; 248/562, 636–638
See application file for complete search history.

(56) References Cited

U.S. PATENT DOCUMENTS 4,960,341 A * 10/1990 Aarre et al. ............... 403/24
5,473,657 A   12/1995 McKenna
(Continued)

FOREIGN PATENT DOCUMENTS

JP  2001286463     10/2001
JP  2006046643 A   2/2006
(Continued)

OTHER PUBLICATIONS

Preliminary Amendment cited in U.S. Appl. No. 14/130,044 dated Dec. 30, 2014, 11 pgs.
(Continued)

Primary Examiner — Anastasia Midkiff
(74) Attorney, Agent, or Firm — Cooper Legal Group, LLC

(57) ABSTRACT

One or more techniques and/or apparatuses described herein provide a roller truck comprising non-rotating dampening material that is configured to dampen vibrations and mitigate the transference of vibrations from a rotating gantry to a support frame and vice-versa during rotation of the rotating gantry relative to the support frame. It will be appreciated that two different types of roller trucks, base roller trucks and z-axis roller trucks, are described herein, and the non-rotating dampening material may be inserted into one or both types of roller trucks. While the instant disclosure finds particular application in the context of computed tomography apparatus, the instant disclosure is not intended to be limited to such applications.

20 Claims, 7 Drawing Sheets

(51) Int. Cl.
*A61B 6/00* (2006.01)
*F16C 19/52* (2006.01)
F16C 19/50 (2006.01)
F16C 27/06 (2006.01)
F27B 7/22 (2006.01)
A61B 6/03 (2006.01)

(52) U.S. Cl.
CPC . *H05G 1/02* (2013.01); *A61B 6/035* (2013.01); *F16C 19/507* (2013.01); *F16C 27/066* (2013.01); *F27B 2007/2286* (2013.01); *Y10T 29/49826* (2015.01)

(56) References Cited

U.S. PATENT DOCUMENTS

| | | | |
|---|---|---|---|
| 5,473,876 | A | 12/1995 | Mann et al. |
| 5,851,327 | A | 12/1998 | Landin |
| 6,823,037 | B2 | 11/2004 | Riemer et al. |
| 2002/0146088 | A1 | 10/2002 | Riemer et al. |
| 2009/0245711 | A1* | 10/2009 | Hattori et al. ............ 384/572 |
| 2011/0247922 | A1* | 10/2011 | Horling et al. ........... 198/843 |
| 2012/0148013 | A1* | 6/2012 | Zhang et al. ............. 378/4 |

FOREIGN PATENT DOCUMENTS

| | | | |
|---|---|---|---|
| JP | 2007048726 | A | 2/2007 |
| JP | 2009046643 | A | 3/2009 |
| JP | 2009510400 | A | 3/2009 |
| JP | 2011024866 | A | 2/2011 |

OTHER PUBLICATIONS

Int. Search Report cited in PCT Application No. PCT/US2011/042567 dated Mar. 15, 2012, 11 pgs.
Korean Office Action cited in Japanese Application No. 2014-518519 dated Mar. 3, 2015, 4 pgs.
"Iterative Filtered Backprojection Methods for Helical Cone-beam CT", Johan Sunnegardh, Aug. 2009, Linkoping University Electronic Press, Linkoping, XP055018986, Chapter 2, sec. 2.2, "Weighted filtered backprojection" Chapter 5, Regularized iterative weighted filtered backprojection, 180 pgs.
"Iterative Methods for Image Reconstruction", Jeffrey A. Fessler, May 14, 2008, ISBI 2006 Tutorial, reprinted from the Internet at: http://web.eecs.umich.edu/~fessler/papers/files/talk/06/isbi,p1,note.pdf, 79 pgs.
"Practical cone-beam algorithm", L.A.Feldkamp, L.C. Davis and J.W. Kress, Feb. 28, 1984, J. Opt. Soc. Am. vol. 1, No. 6, 8 pgs.
Korean Office Action cited in Japanese Application No. 2014-518517 dated Mar. 3, 2015, 4 pgs.
International Search Report cited in related application No. PCT/US11/42567 dated Mar. 15, 2012, pp. 11.

* cited by examiner

VIBRATION DAMPING FOR APPARATUS COMPRISING ROTATING GANTRY

BACKGROUND

The present application relates to a roller truck for supporting a rotating object relative to a stationary object and/or for facilitating rotation of the rotating object relative to the stationary object. It finds particular application in the context of computed tomography (CT) scanners, such as might be used in medical, security, and/or industrial applications, for supporting a rotating gantry (e.g., comprising an x-ray source and a detector array) that rotates relative to a stationary portion of a CT scanner. For example, a roller truck may be positioned between a support frame (e.g., a stationary member) and a rotating gantry and may be configured to support the mass of the rotating gantry and/or to facilitate rotation of the rotating gantry relative to the support frame. It also relates to other applications where supporting a rotating object may be useful.

A typical CT scanner comprises a rotating gantry comprising a central opening (e.g., a bore) large enough to receive an object (e.g., a patient, luggage, etc.) extending along a scanning axis, and the rotating gantry is rotated about the object during an examination procedure. An x-ray source is positioned on the rotating gantry substantially diametrically across the central opening from a detector array. As the rotating gantry rotates, the x-ray source emits x-rays that traverse the object and are detected by the detector array. By rotating the x-ray source about the scanning axis and relative to the object, x-rays are projected through the object from a plurality of different directions. An image of an examined portion of the object can then be constructed from data yielded from the detected x-rays.

Because undesirable vibrations of the CT scanner during an examination can cause faulty or erroneous image information, the structure of the scanner (e.g., the rotating gantry and the support frame) typically comprises massively reinforced components often weighing a ton or more in an effort to reduce mechanical noise. Consequently, because of the weight, the rotating gantry has usually been supported in the frame by an expensive and heavy precision roller bearing or ball bearing assembly (e.g., sometimes referred to by those skilled in that art as a tank turret bearing).

Many of the disadvantages inherent in such massive, expensive, relatively fixed CT scan structures were recognized and addressed, at least in part, by the apparatus disclosed in U.S. Pat. No. 4,928,283 issued May 22, 1990 to Gordon, which is assigned to the assignee of the present disclosure. In the aforesaid '283 patent, Gordon broadly suggests the use of rollers rather than bearings for rotatably supporting the rotating gantry in a support frame, without however discussion of the nature and characteristics of such rollers.

U.S. Pat. No. 5,473,657 issued Dec. 5, 1995 to McKenna, which is also assigned to the assignee of the present disclosure, discloses an improved x-ray tomography structure comprising a support frame configured to support the rotating gantry. The mass of the rotating gantry rests on one or more resilient rollers so that the top half of the rotating gantry is substantially unconstrained (e.g., for centerless rotation) so as to allow the rotating gantry to expand and contract while introducing little to no error-producing stresses into the rotating gantry and/or support frame. The one or more rollers are mounted in a truck that is generally supported about a pivot axis. The resilient rollers serve to dampen the transfer of vibrations to the rotating gantry as it rotates and/or accommodate temperature cycling of the rotating gantry.

While the '657 patent provided significant cost and weight benefits over the use of bearings, the rotation of the rotating gantry and/or minor imperfections in the rollers and/or rotating gantry continued to generate and/or transfer vibrations, or vibration frequencies, which could potentially interfere with the operational frequencies of the CT scanner and which could result in degradation to images yielded from a CT examination. Additionally, it was determined that the ability of the rollers to dampen the transfer of vibrations was limited because the amount of energy required to move the rotating gantry directly depended upon the dampening (e.g., the greater the dampening, the more energy required).

In U.S. Pat. No. 6,823,037 issued Nov. 23, 2004 to Riemer et al., which is also assigned to the assignee of the present disclosure, it was purposed that the vibration frequencies be shifted to frequency ranges in which the CT scanner normally did not operate. To do this, two or more roller trucks were proposed, with at least one of the trucks comprising a spring plate and at least another of the trucks not comprising the spring plate. In this way, the vibration frequencies of the CT scanner would be less likely to interfere with the operational frequencies of the CT scanner, for example.

However, merely shifting vibration frequencies may be inadequate for current performance expectations of CT scanners. For example, 20 years ago, the CT scanners generally operated at merely one or two relatively slow speeds, or frequencies. Today, CT scanners are expected to rotate at much higher RPMs and, in some applications, a single CT scanner may be expected to rotate at a plurality of different speeds (e.g., within a wide range of RPMs). Thus, it has become difficult to shift the vibration frequencies to a frequency range that will not interfere, or will not substantially interfere, with the operational frequencies of the CT scanner.

SUMMARY

Aspects of the present application address the above matters, and others. According to one aspect, an apparatus is provided. The apparatus comprises a support frame and a rotating gantry configured for rotation relative to the support frame. The apparatus also comprises a roller truck configured to at least partially support the rotating gantry and facilitate rotation of the rotating gantry relative to the support frame. The roller truck comprises a non-rotating dampening material for dampening vibrations caused by the rotation of the rotating gantry.

According to another aspect, a method for constructing a roller truck for supporting a rotating gantry and for allowing for rotation of the rotating gantry relative to a support frame is provided. The method comprises attaching one or more rollers to one or more roller axles and coupling the one or more roller axles to a plate. The method also comprises coupling an attachment member to the plate, the attachment member configured to operably couple the roller truck to at least one of the rotating gantry and the support frame. The method also comprises inserting a non-rotating dampening material into the roller truck, the non-rotating dampening material configured to dampen vibrations caused by the rotation of the rotating gantry relative to the support frame.

According to yet another aspect, a computed tomography (CT) apparatus is provided. The CT apparatus comprises a support frame and a rotating gantry. The rotating gantry is configured for rotation relative to the support frame and comprises an x-ray source and a detector array. The CT apparatus also comprises a roller truck configured to support the rotating gantry and to allow the rotating gantry to rotate relative to the support frame. The roller truck comprises a non-rotating dampening material configured to dampen vibrations caused by the rotation of the rotating gantry relative to the support frame.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
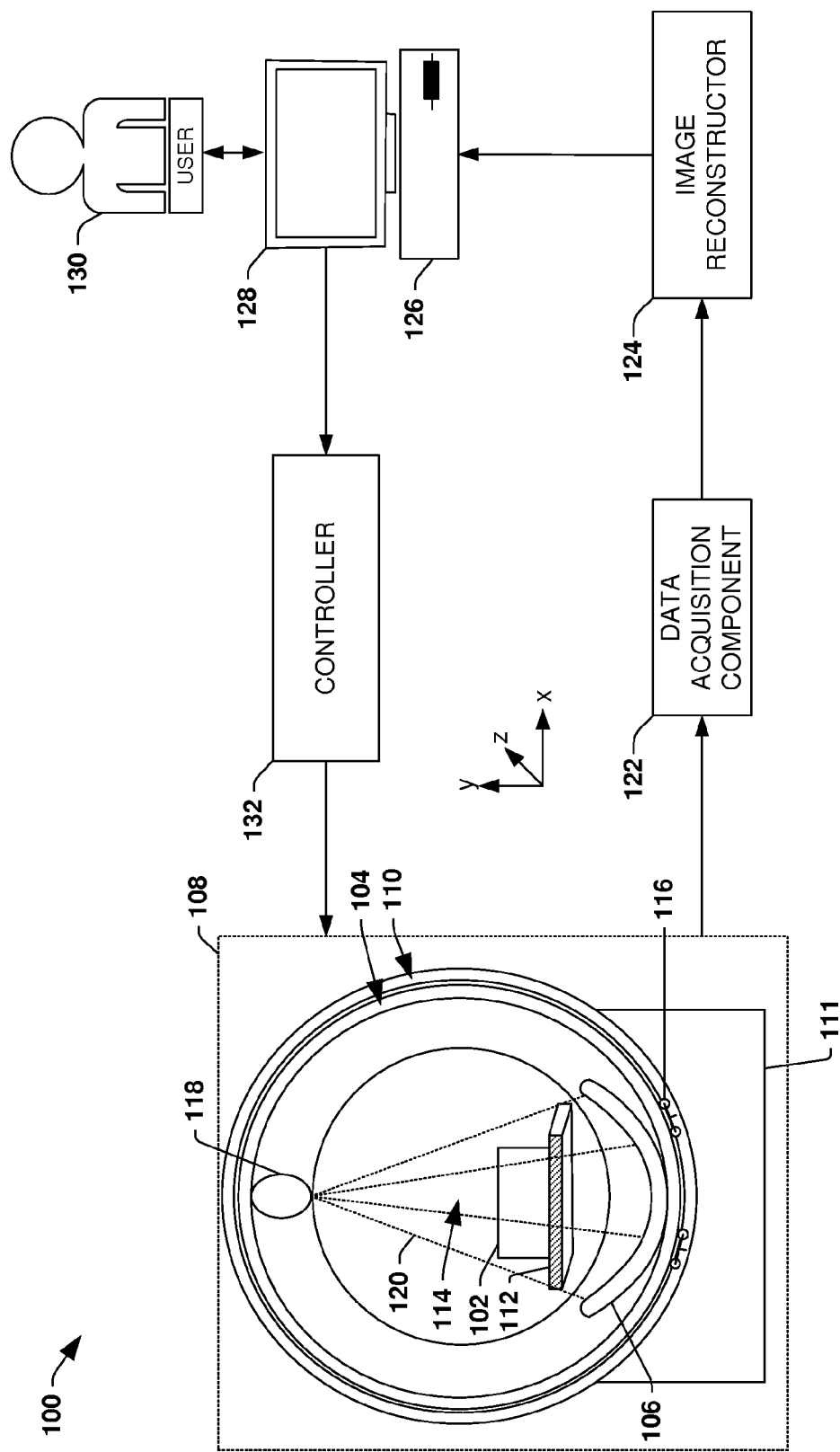
FIG. 1 is a schematic block diagram illustrating an example environment for using a roller truck such as described herein.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a roller truck comprising a non-rotating dampening material inserted into the roller truck and configured to dampen vibrations, or vibration frequencies, yielded from the rotation of a rotating gantry. The roller truck is generally coupled (e.g., fastened) to a support frame (e.g., a stationary support member) and is configured to at least partially support the rotating gantry during rotation. For example, a roller truck may be configured to mitigate movement of the rotating gantry in a z-dimension (e.g., coming into and/or out of the page in FIG. 1) and/or may be configured to at least partially support the mass of the rotating gantry. Moreover, in one embodiment, one or more of the roller trucks may comprise a drive shaft, for example, and may be configured to rotate the rotating gantry relative to the support frame and/or an object under examination. It will be appreciated that while continued reference is made to a roller truck of a CT scanner (e.g., such as may be used in medical, security, and/or industrial applications), the apparatuses and/or methods described herein are not intended to be so limited. That is, the apparatuses and/or methods described herein may be used for other applications (e.g., besides CT applications) where supporting a rotating member and/or rotating the member relative to a stationary member may be useful, for example.

It will be appreciated that for purposes of clarity and understanding, the non-rotating dampening material aspects of the roller trucks are shaded in at least some of the example figures. It will also be appreciated that while the figures illustrate several example locations where non-rotating dampening material may be inserted into a roller truck, the instant disclosure, including the claims, is not intended to be limited as such to the extent practicable. That is, in addition to and/or in substitution for the locations described herein, the non-rotating dampening material may be inserted into other areas of the roller trucks that are not mentioned herein but would be readily apparent to those skilled in the art. It will be appreciated that numerous considerations, such as available space for the non-rotating dampening material, design modifications required to insert the non-rotating dampening material in a particular location, the properties of the non-rotating dampening material that is selected, and/or other practical considerations may affect the placement of the non-rotating dampening material, for example.

FIG. 1 is an illustration of an example environment 100 in which a roller truck as described herein may be useful. More particularly, FIG. 1 illustrates an example computed tomography (CT) apparatus that can be configured to acquire volumetric information regarding an object 102 under examination and generate two-dimensional and/or three-dimensional images therefrom. It will be appreciated that the example environment 100 merely illustrates an example schematic and is not intended to be interpreted in a limiting manner, such as necessarily specifying the location, inclusion, and/or relative arrangement of the components described herein. For example, a data acquisition component 122 as illustrated in FIG. 1 may be part of a rotating gantry 104 portion of the examination apparatus, or more particularly may be part of a detector array 106, for example.

In the example environment 100, an object examination apparatus 108 is configured to examine one or more objects 102 (e.g., a series of suitcases at an airport, a patient, etc.). The object examination apparatus 108 can comprise a rotating gantry 104 and a (stationary) support structure 110 that is supported on a base 111. During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated about the object(s) 102 by a roller truck 116 comprising a component configured to rotate the rotating gantry, such as a motor, drive shaft, chain, etc.

The rotating gantry 104 may surround a portion of the examination region 114 and may comprise one or more radiation sources 118 (e.g., an ionizing x-ray source) and a detector array 106, which may also be referred to herein as merely a detector, that is mounted on a substantially diametrically opposite side of the rotating gantry 104 relative to the radiation source(s) 118.

During an examination of the object(s) 102, the radiation source(s) 118 emits fan, cone, wedge, and/or other shaped radiation 120 configurations into the examination region 114 of the object examination apparatus 108. It will be appreciated to those skilled in the art that such radiation 120 may be emitted substantially continuously and/or may be emitted intermittently (e.g., a short pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 configured to compile signals that were transmitted within a predetermined time interval, or measurement interval, using techniques known to those skilled in the art (e.g., binning, integration, etc.). It will be appreciated that such a measurement interval may be referred to by those skilled in the art as a "view" and generally reflects signals generated from radiation 120 that was emitted while the radiation source(s) 118 was at a particular angular range relative to the object 102. Based upon the compiled signals, the data acquisition component 122 can generate projection data indicative of the compiled signals, for example.

The example environment 100 further comprises an image reconstructor 124 configured to receive the projection data that is output by the data acquisition component 122. The image reconstructor 124 is configured to generate image data from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 also includes a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive user input from the terminal 126 and generate instructions for the object examination apparatus 108 indicative of operations to be performed. For example, the user 130 may want to reexamine the object(s) 102, and the controller 132 may issue a command instructing the support article 112 to reverse direction (e.g., bringing the object(s) 102 back into an examination region 114 of the object examination apparatus 102).

Figure 2:
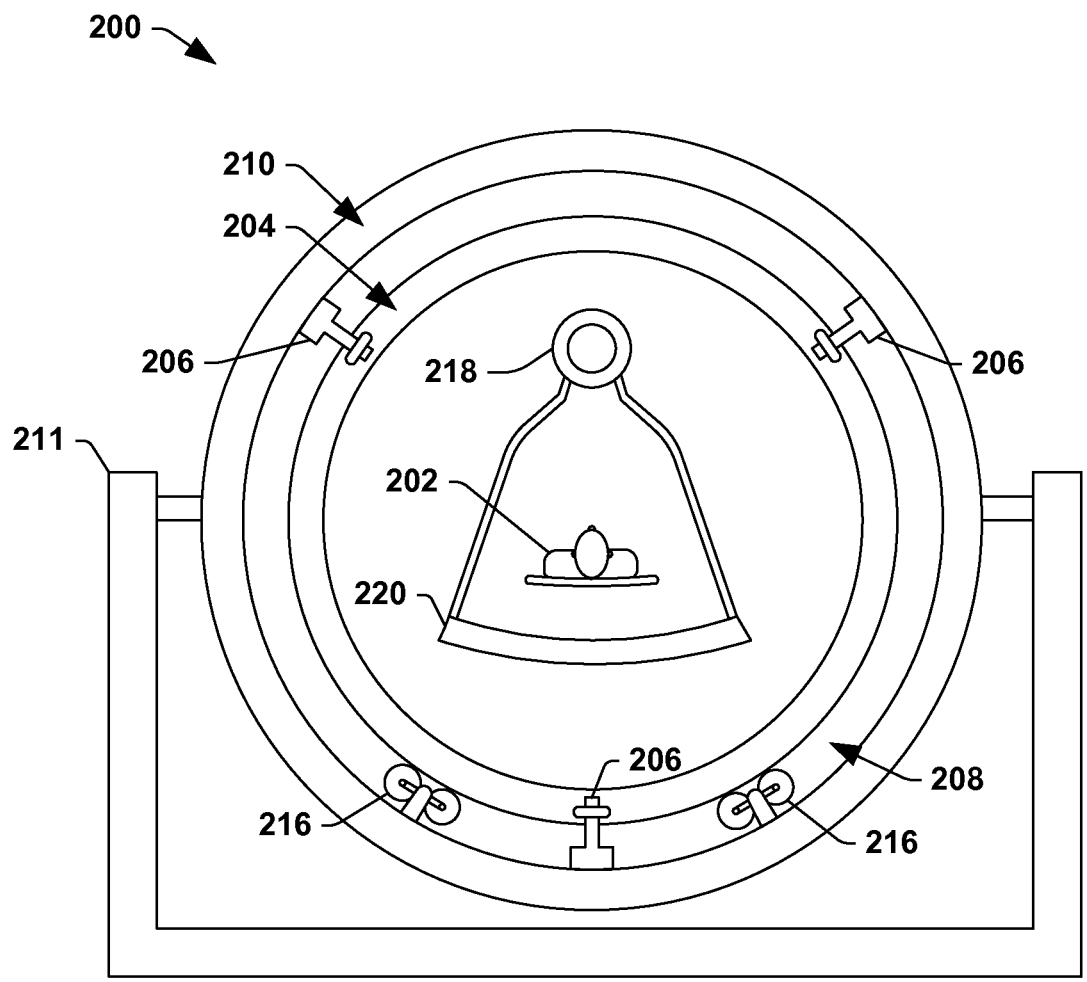
FIG. 2 illustrates an example object examination apparatus comprising a rotating gantry supported on a support frame by a roller truck.

FIG. 2 is a closer view of an object examination apparatus 200 (e.g., 108 in FIG. 1). It will be appreciated that while the object examination apparatus illustrated in FIG. 2 illustrates a patient 202 being examined by the object examination apparatus 200 (e.g., the CT scanner), other objects, such as animals, briefcases, luggage, lumber, etc. may also be examined by the object examination apparatus 200.

As illustrated, the object examination apparatus 200 comprises a rotating gantry 204 (e.g., 104 in FIG. 1) and a support frame 210 (e.g., 110 in FIG. 1) that is mounted, optionally pivotally mounted, on a base 211 (e.g., 111 in FIG. 1). Roller trucks generally support the rotating gantry 204 relative to the support frame 210, which is typically stationary. It will be appreciated that as used herein, there are essentially two types of roller trucks. Z-axis roller trucks 206 generally support the rotating gantry 204 from tilting in the z-dimension (e.g., into and/or out of the page) and contact a side periphery of the rotating gantry, while base roller trucks 216 (e.g., 116 in FIG. 1) generally support the mass of the rotating gantry 204. (e.g., although the base roller trucks 216 may at least partially assist in mitigating the rotating gantry 204 from tilting in the z-dimension) and contact an outer periphery (perpendicular to the side periphery) of the rotating gantry. That is, the mass of the rotating gantry 204 is substantially supported by the base roller trucks 216, with the top half of the rotating gantry 204 substantially unconstrained in a rotation plane and mounted for rotation relative to support frame 210, for example.

Typically, the support frame 210 and the rotating gantry 204 are dimensioned so that the rotating gantry 204 is rotatably supported on the base roller trucks 216 to provide an annular space 208 yielding ample clearance between the outer periphery of the rotating gantry 204 and the inner periphery of the support frame 210 so that the rotating gantry 204 is free to expand and contract as it heats and cools, for example. Preferably, at least two base roller trucks 216 are pivotally mounted on the support frame 210 and at least six z-axis roller trucks 206 (e.g., three on a front side and 3 on a back side) are mounted on the support frame 210, but greater or fewer base roller trucks 216 and/or z-axis roller trucks 206 are contemplated herein. Generally, where the object examination apparatus 200 comprises at least two base roller trucks 216, the base roller trucks 216 are symmetrically positioned on opposite sides of a vertical center line and the z-axis roller trucks 206 are spaced substantially evenly about the support frame 210. Although not shown, at least one of the base roller trucks 216 can be provided with a motor for turning one or more rollers of the base roller truck(s) 216 for rotating the rotating gantry 204, for example.

It will be appreciated that while FIG. 2 illustrates the roller trucks as mounted to the support frame 210, in another embodiment, one or more of the base roller trucks 216 and/or one or more of the z-axis roller trucks 206 may be mounted, or operably coupled, to the rotating gantry 204 and the rollers of respective roller trucks (operably coupled to the rotating gantry 204) may make contact with the support frame, for example.

As will be described in more detail below, one or more of the z-axis roller trucks 206 and/or one or more of the base roller trucks 216 comprise a non-rotating dampening material and are configured to dampen vibrations caused by the rotation of the rotating gantry 204. That is, in addition to and/or in substitution for rollers that comprise a dampening material, one or more of the roller trucks may comprises a non-rotating dampening material. For example, in one embodiment, one or more of the base roller trucks 216 comprise a dampening material. In another embodiment, one or more of the z-axis roller trucks 206 comprise a dampening material. It will be appreciated that as used herein, the terms dampening material generally refer to a material that substantially mitigates vibration frequencies. For example, fiberglass, vinyl, doped plastics, fiberglass concrete dipped in resin and/or butyl rubber generally have properties that cause such materials to mitigate vibration frequencies. Such materials may also be referred to by those skilled in the art as dead materials because of their ability to absorb impact or vibrations while mitigating the transference of the impact or vibrations to other materials operably coupled to the dead material (e.g., the impact or vibrations are converted into heat (or other) energy as opposed to transferred as mechanical oscillations). It will also be appreciated that in a CT application, the non-rotating dampening material dampens the natural resonance caused by the rotation of the rotating gantry 204 to mitigate distortions in reconstructed images produced by a CT scanner.

The example object examination apparatus 200 further comprises an x-ray source 218 (e.g., 118 in FIG. 1) and a detector array 220 (e.g. 106 in FIG. 1), which are mounted to the rotating gantry 204 for rotational motion about the patient 202 (e.g., or other object). As was described with respect to FIG. 1, as radiation or x-rays are emitted from the x-ray source 218, the rotating gantry 204, including the x-ray source 218 and the detector array 220, rotates relative to the support frame 210 (e.g., via at least one of the base roller trucks 216). The base roller trucks 216 comprise rollers that make contact with the rotating gantry 204 and at least partially support the mass of the rotating gantry 204. The z-axis roller trucks 206 also respectively comprise at least one roller that makes contact with the rotating gantry 204 and supports the rotating gantry from tilting in the z-dimension (e.g., so that the rotating gantry remains substantially within a rotational plane). It will be appreciated that while merely a front side of the object examination apparatus 200 is illustrated herein. If the object examination apparatus 200 were viewed from a back side, opposite the front side, an additional three z-axis roller trucks 206 may be seen, for example.

Figure 3:
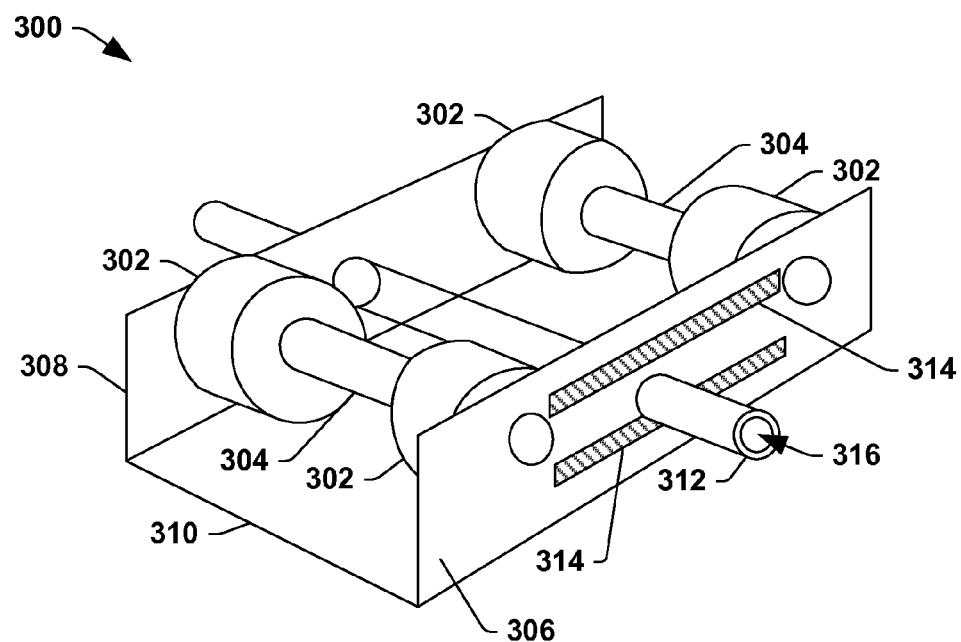
FIG. 3 illustrates an example base roller truck comprising a non-rotating dampening material.
Figure 4:
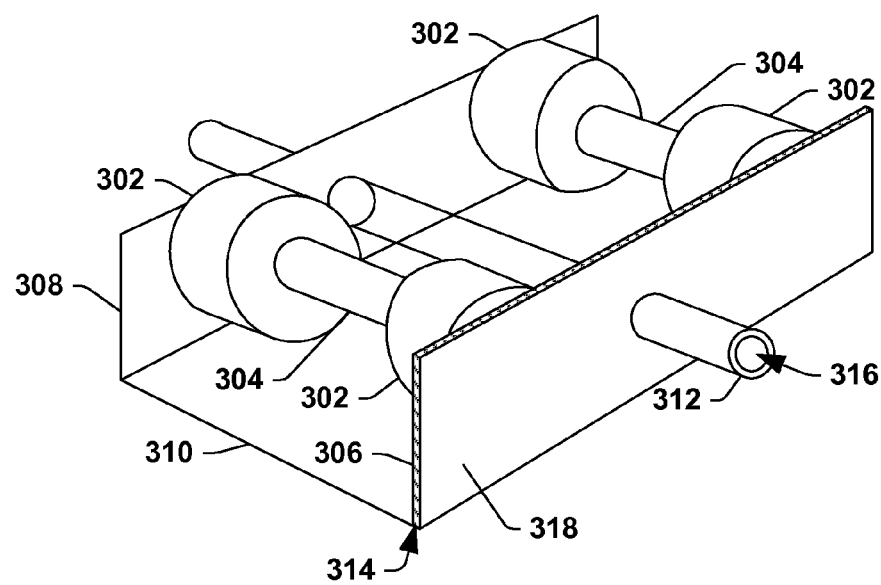
FIG. 4 illustrates an example base roller truck comprising a non-rotating dampening material.
Figure 5:
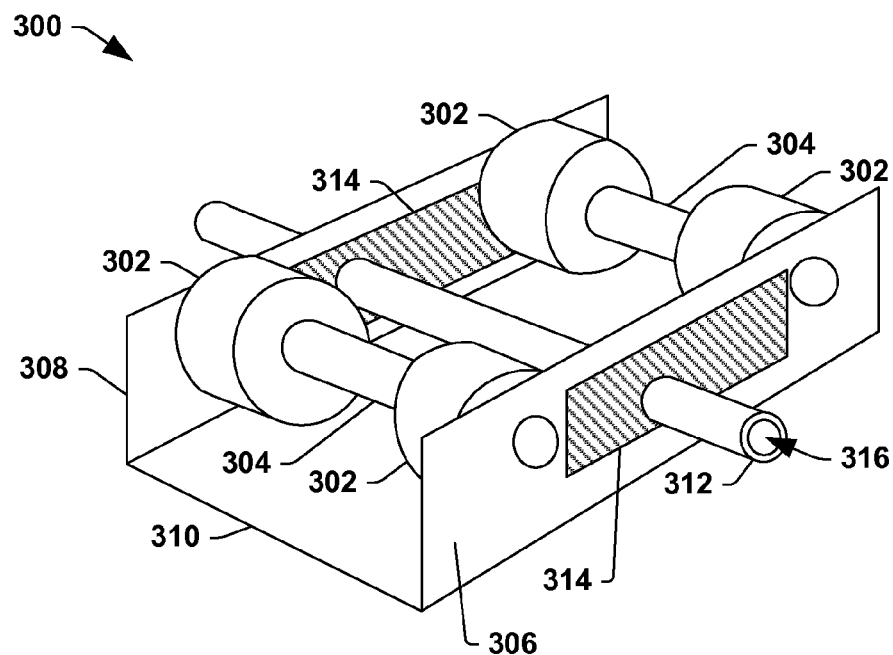
FIG. 5 illustrates an example base roller truck comprising a non-rotating dampening material.

FIGS. 3-5 illustrate example embodiments of a base roller truck 300 (e.g., 216 in FIG. 2) configured to support the mass of a rotating gantry (e.g., 204 in FIG. 2) and/or to facilitate rotation of the rotating gantry relative to a support frame (e.g., 210 in FIG. 2). Moreover, optionally, the base roller truck 300 may be operably coupled to a motor (not shown) configured to provide power to at least one roller axle 304 of the base roller truck 300. In this way, the base roller truck 300 can rotate the rotating gantry relative to the support frame, for example. Zero or more remaining rollers 302 of the roller truck 300 that are not operably coupled to the motor can be simply follower, idler or free-running driven rollers, for example.

As illustrated in the example figures, the base roller truck 300 comprises at least one (e.g., but preferably two or more) rollers 302 rotatable in a common plane, parallel to or coplanar with a scanning plane (e.g., such that the rollers roll from left-to-right or right-to-left in the object examination apparatus 200 illustrated in FIG. 2). In one embodiment, as illustrated, the base roller truck 300 is comprised of two side-by-side, parallel pairs of rollers; however, other embodiments are contemplated herein. For example, in another embodiment, the base roller truck 300 is comprised of merely two rollers in parallel. The respective rollers 302 are mounted on their own roller axles 304 (e.g., such that no two rollers share a common roller axle). Additionally or alternatively, two or more rollers 302 may be mounted on a single, common roller axle, for example.

Respective rollers 302 are configured to contact the rotating gantry (e.g., to support and/or rotate the rotating gantry) and are generally comprised of a resilient material, such as rubber, nylon, or suitable polymer, for example. Characteristics that may be consider when selecting a suitable material may include, for example, the ability of the material to dampen mechanical noise and/or the degree of compression in the roller when the mass of the rotating gantry is supported by the roller 302. In one embodiment, it is preferable that the rollers 302 respectively comprise a material that has a high degree of dampening capability (e.g., so that a greater amount of mechanical noise is dampened) and has a low degree of compression (e.g., so that less energy is required to rotate the roller 302). Moreover, the ability of the material to accommodate thermal expansion of the rotating gantry may also be considered when selecting a suitable material for the rollers 302. It will also be appreciated that rollers 302 as described herein, are not the equivalent of roller bearings, inasmuch as the operation of roller bearings involve substantial metal-to-metal contact, whereas the rollers are generally comprised of a nonmetal and/or a metalloid, for example.

The base roller truck 300 further comprises substantially parallel side walls 306, 308 joined by a bottom plate 310. Respective roller axles 304 are operably coupled to one or both of the side walls 306, 308 of the base roller truck 300. Moreover, in one embodiment, an attachment member 312 extending through the base roller truck 300 (e.g., preferably centrally) is configured to be operably coupled to the support frame and/or the rotating gantry of the object examination apparatus. For example, the attachment member 312 may be configured to be coupled to the support frame (e.g., 210 in FIG. 2) such that the roller truck is supported by the support frame, and the rotating gantry (e.g., 204 in FIG. 2) is supported by the rollers. Thus, the mass of the rotating gantry may be supported by the support frame via the attachment member 312, for example.

The attachment member 312 is preferably tubular and may comprise an axial bore 316 for rotatably receiving a pin or bolt (not shown), for example, which can be operably coupled to the support frame. In one embodiment, a bushing (not shown) can be provided in the bore 316 of the attachment member 312. Thus, in at least one embodiment, the attachment member 312 is configured to allow the base roller truck 300 to pivot about an axis of the attachment member 312, for example. The attachment member 312 may alternatively be provided as a pin and rotatably received in bearings or other suitable mounts of the support frame (e.g., or rotating gantry), for example.

The side walls 306, 308 and/or the bottom plate 310 of the base roller truck 300 may be comprised of a plastic, sheet metal, or other elastically complaint material, for example. Moreover, in one embodiment as illustrated in FIG. 3, at least some of at least one side wall 306 of at least one base roller truck 300 comprises a non-rotating dampening material 314 inserted into cutouts along the side wall 306 between the roller axles 304 (e.g., between a first roller axle and a second roller axle). The dampening material 314 is configured to absorb vibrational frequencies generated by the rotation of the rotating gantry and/or to mitigate the transfer of vibration frequencies from the rotating gantry to the support frame via the attachment member 312, for example. That is, when the side wall 306 of the base roller truck 300 attempts to flex and/or when the attachment member 312 attempts to flex, the flexing motion is dampened and/or impaired by the dampening material 314 inserted into the cutouts along the side wall 306 (e.g., mitigating the transfer of vibration frequencies from the base roller truck 300 to the support frame and/or vice-versa).

In another embodiment, as illustrated in FIG. 4, non-rotating dampening material 314 may be attached (e.g., adhered, fastened, or otherwise coupled) to at least one sidewall 306 of at least one base roller truck 300. Moreover, an additional plate 318 may be adhered to an opposite side of the non-rotating dampening material 314 relative to the sidewall 306 (e.g., creating a sandwich design). When the sidewall 306 attempts to flex, bend, distort, etc., the energy is absorbed or otherwise mitigated by the dampening material 314 to mitigate the amount and/or degree of energy transferred from the rollers 302 to the support member and/or vice-versa.

It will be appreciated that FIG. 4 illustrates merely one embodiment of an example sandwich design and other similar embodiments are also contemplated. For example, the dampening material may be attached to any one or more portions of the sidewalls 306 and/or 308 and/or to the bottom plate 310 of the base roller truck 300. In one example, the base roller truck 300 is formed from two metal plates respectively substantially forming a "U" shape, where (e.g., portions(s) of) the two metal plates are separated from one another via non-rotating dampening material. Moreover, it will be appreciated that while FIG. 4 appears to show the dampening material as extending across the entire surface of the sidewall 306 and/or plate 318, it will be appreciated that the dampening material may merely cover one or more portions of the surface area of the sidewall 306 and/or plate 318 (e.g., such that there are one or more voids (e.g., pockets of air) between the sidewall 306 and the plate 318), for example.

In yet another embodiment, as illustrated in FIG. 5, the attachment member 312 is separated from the roller axle 304 on both side walls 306, 308 by a non-rotating dampening material 314 configured to absorb vibrational frequencies generated by the rotation of the rotating gantry and/or to mitigate the transfer of vibration frequencies from the rotating gantry to the support frame via the attachment member 312, for example. Stated differently, the non-rotating dampening material 314 substantially surrounds the attachment member. In this way, vibration frequencies would be required to pass through the dampening material 314 to be transferred from the rotating gantry and/or from the base roller truck 300 to the support frame via the attachment member 312, for example.

It will be appreciated the while FIG. 3-5 illustrates several examples for inserting and/or placing non-rotating dampening material 314 in a base roller truck 300 comprising sidewalls 306, 308 and/or a base plate 310, numerous variations regarding the placement and/or amount are also contemplated. That is, the non-rotating dampening material is generally sized to allow the vibration frequencies to be converted into heat (or other) energy that can be dissipated (e.g., naturally or otherwise) into the air and/or converted into electrical energy, for example, to be used to at least partially supply power to the object examination device, for example. Consideration may be made to provide for an adequate amount of material to sufficiently dampen the vibrations (e.g., by converting the mechanical energy into heat) to mitigate (e.g., to substantially zero) the amount and/or severity of the vibrations that pass through the dampening material and are transferred from the rotating gantry to the support frame and/or vice-verse, for example. Thus, the amount and/or location of the non-rotating dampening material may be application specific, and FIGS. 3-5 are not intended to limit the scope of the instant disclosure, including the appended claims, to merely the examples illustrated.

Moreover, it will be appreciated that while FIGS. 3-5 illustrates the attachment member 312 as extending through the base roller truck 300 (e.g., such that the attachment member passes through both sidewalls 306, 308), in another embodiment, the attachment member 312 does not extend through the base roller truck 300. For example, a first attachment member may be operably coupled to a first sidewall 306 and a second attachment member may be operably coupled to a second sidewall 308 (e.g., and/or to another plate (e.g., 318 in FIG. 4) separated from a sidewall 306 by non-rotating dampening material 314.

Figure 6:
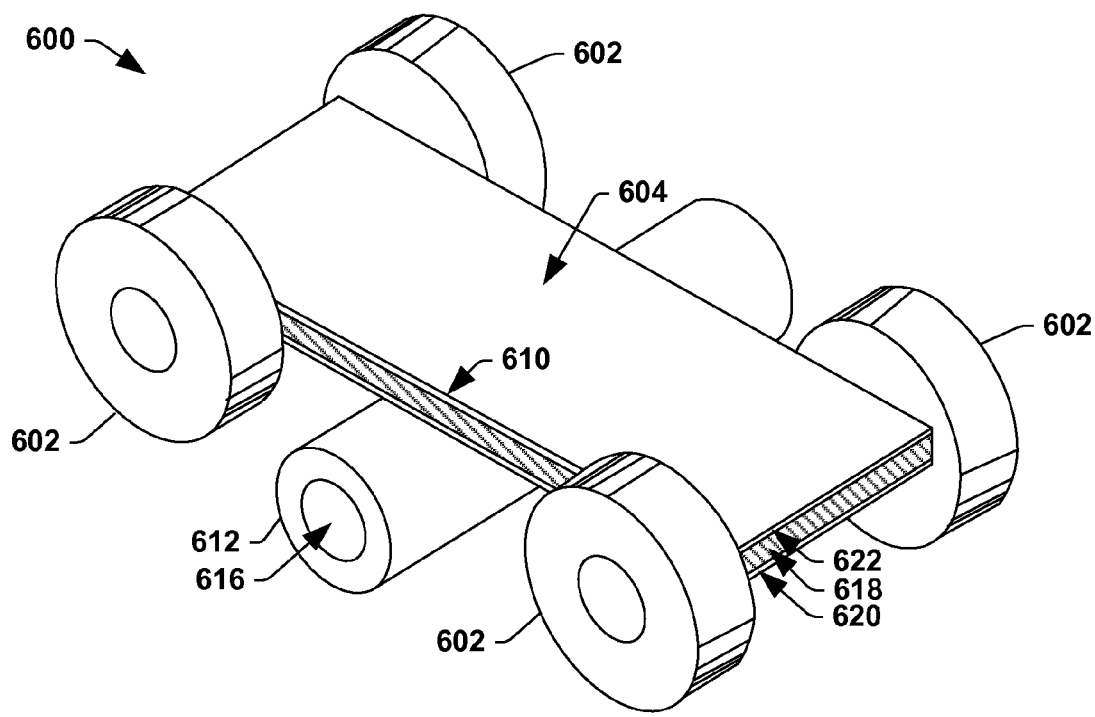
FIG. 6 illustrates an example base roller truck comprising a non-rotating dampening material.

FIG. 6 illustrates yet another example a base roller truck 600 (e.g., 216 in FIG. 2) configured to support a rotating gantry (e.g., 204 in FIG. 2) and comprising a non-rotating dampening material for mitigating the transfer of vibrations from the rotating gantry to a support frame (e.g., 210 in FIG. 2) and/or for mitigating the transfer of vibrations from the support frame to the rotating gantry, for example. The base roller truck 600 comprises an attachment member 612 (e.g., 312 in FIGS. 3-5) and at least one roller axle (not shown) operably coupled to a plate 610.

The roller axle(s) (e.g., which respectively connect a roller(s) 602 (e.g., 302 in FIG. 3) to the plate 610) are operably coupled (e.g., mounted) to at least one of a top surface 604 and a bottom surface (e.g., opposite the top surface 604), and the attachment member 612 is operably coupled to at least one of the bottom surface and the top surface 604 of the plate 610, generally between two roller axles. It will be appreciated that while FIG. 6 illustrates the roller axles and the attachment member respectively being operably coupled to the same surface of the plate 610 (e.g., the bottom surface), the roller axles and the attachment member 612 may be respectively connected to different surfaces. Moreover, one or more roller axles may be connected to a different surface than other roller axles of the base roller truck 600, for example.

As described with respect to FIGS. 3-5, the attachment member 612 is for operably coupling the roller truck 600 to at least one of the support frame and the rotating gantry. In one embodiment (e.g., as shown), the attachment member 612 is tubular and includes an axial bore 616 (e.g., 316 in FIG. 3) for rotatably receiving a pin or bolt (not shown), for example, which can then be operably coupled to the support frame, for example. A bushing (not shown) can be provided in the bore 616 of the attachment member 612. Alternatively, in another embodiment, the attachment member 612 may be provided as a pin and rotatably received in bearings or other suitable mounts of the support frame (e.g., or rotating gantry), for example.

One or more rollers 602 are rotatably mounted on respective roller axles and are configured to support the rotating gantry and allow the rotating gantry to rotate with respect to the support frame. It will be appreciated that as described above, two or more rollers 602 may, in one embodiment, share a common roller axle, or, alternatively, respective rollers 602 may be operably coupled to a respective roller axle (e.g., such that no two rollers 602 share a common roller axle).

In one embodiment, the plate 610 is comprised of two or more layers, with at least one layer comprising a non-rotating dampening material. For example, in FIG. 6, the plate 610 is comprised of three layers, with the middle layer 618 being comprised of a non-rotating dampening material such as a strong and durable, yet resiliently flexible material. For example, in one embodiment, the outer layers 620, 622 may be comprised of a steel or aluminum while the middle layer 618 is comprised of a vinyl or fiberglass resin, for example. In this way, vibrations passing through the base roller truck 600 may be absorbed or dampened by the middle layer 618, for example.

It will be appreciated that in one embodiment where the plate 610 is comprised of a plurality of layers, including a layer comprised of a non-rotating dampening material, the roller axles may be positioned on a surface opposite that of the attachment member 612. For example, if the roller axles are attached to a bottom surface, the attachment member may be operably coupled to the top surface 604. Conversely, if the roller axles are operably coupled to the top surface 604, the attachment member 612 may be operably coupled to the bottom surface, for example. In this way, the transfer of vibrations between the rollers 602 and the support frame is mitigated because the vibration frequencies would be required to pass through the non-rotating dampening material, for example. While three layers are illustrated herein, additional and/or fewer layers are contemplated. For example, in one embodiment, the plate 610 is comprised of five layers, with two layers of dampening material being sandwiched between three layers of non-rotating dampening material. In another embodiment, the plate 610 is merely comprised of two layers, with at least one of the layers comprising a non-rotating dampening material.

It will also be appreciated that the non-rotating dampening materials that are operably coupled to the base roller truck 600 as described herein may be fastened to the base roller truck 600 using an epoxy (e.g., to mitigate the transfer of vibration frequencies through bolts, screws or other fastening mechanisms that may allow vibration frequencies to transfer). For example, in one embodiment, the non-rotating dampening material of the middle layer 618 is operably coupled to one or both of the outer layers 620, 622 using a polyurethane adhesive.

Figure 7:
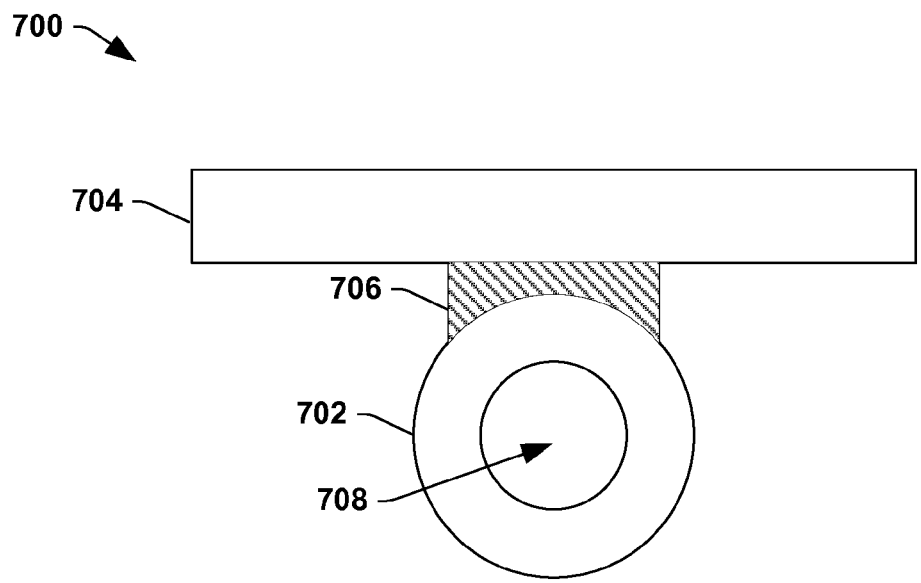
FIG. 7 illustrates a side view of an example attachment member coupled to a plate of a base roller truck, a non-rotating dampening material inserted between the plate and the attachment member.

FIG. 7 illustrates an example environment 700 of an attachment member 702 (e.g., 612 in FIG. 6) that is configured to couple a base roller truck (e.g., 600 in FIG. 6) to a support frame (e.g., 210 in FIG. 2) and/or a rotating gantry. More specifically, FIG. 7 illustrates an example location on a base roller truck wherein non-rotating dampening material 706 can be inserted (e.g., instead of or in conjunction with the insertion of dampening material into the plate 610 in FIG. 6).

As illustrated, the attachment member 702 is tubular and comprises an axial bore 708 (e.g., 316 in FIG. 3) for rotatably receiving a pin or bolt (not shown), which can then be operably coupled to the support frame (e.g., or rotating gantry), for example. A bushing (not shown) can be provided in the bore 708 of the attachment member 702. Alternatively, in another embodiment, the attachment member 702 may be provided as a pin and rotatably received in bearings or other suitable mounts of the support frame (e.g., or rotating gantry), for example.

Between the attachment member 702 and a plate 704 (e.g., 610 in FIG. 6) to which the roller axles are operably coupled, is inserted a non-rotating dampening material 706 that at least partially surrounds the attachment member 702. The non-rotating dampening material 706 is generally sized (e.g. the length, width, and/or thickness of the material) such that vibrations in the plate 704 are not transferred (e.g., or the transference is mitigated) to the attachment member 702 and/or vice-versa.

It will be appreciated that the non-rotating dampening material 706 may be fastened and/or adhered to the plate 704 and/or to the attachment member 702 through an number of ways. For example, in one embodiment, the non-rotating dampening material 706 is adhered to the plate 704 and/or to the attachment member 702 via an adhesive material, such as an epoxy, for example.

Moreover, while FIG. 7 illustrates the non-rotating dampening material 706 as being situated between the plate 704 and the attachment member 702, a similar concept could be used to operably couple a non-rotating dampening material between the plate 704 and a roller axle(s) for one or more rollers (e.g., such that the non-rotating dampening material at least partially surrounds the roller axle). Thus, a non-rotating dampening material may be inserted between the plate 704 and the attachment member 702 and/or between the plate 704 (e.g., or another plate) and a roller axle(s) of one or more rollers, for example.

Figure 8:
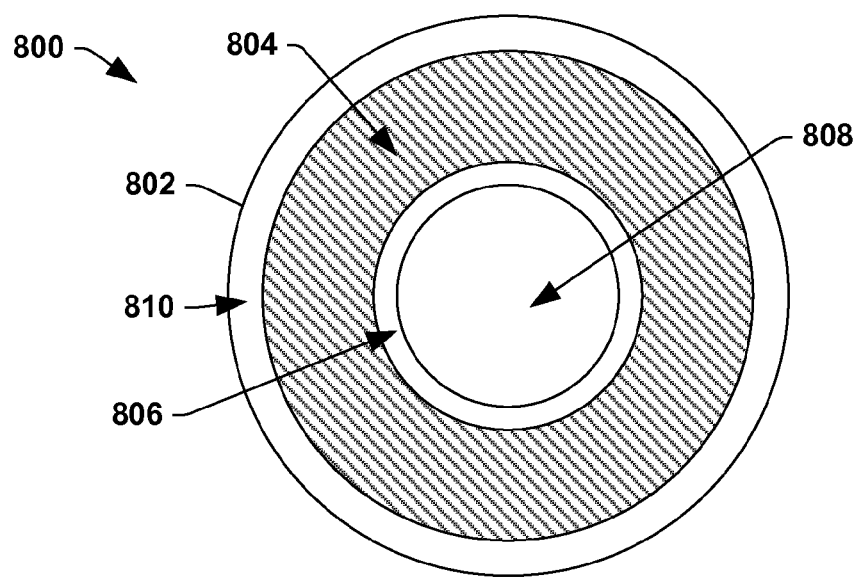
FIG. 8 illustrates a side view of an example attachment member, the non-rotating dampening material inserted into the attachment member.

FIG. 8 illustrates yet another environment 800 for inserting non-rotating dampening material into a base roller truck (e.g., 216 in FIG. 2), such as the base roller trucks 300 illustrated in FIGS. 3-5 and/or 600 illustrated in FIG. 6. More particularly, FIG. 8 illustrates an example attachment member 802 (e.g., 312 in FIG. 3 and 612 in FIG. 6) comprising a plurality of layers, with at least one layer 804 comprising a non-rotating dampening material.

As illustrated, the attachment member 802 comprises three layers (e.g., although the attachment member 802 may comprise fewer or more layers). An inner layer 806 is generally comprised of a substantially rigid material, such as steel, and an inner surface of the inner layer 806 generally defines an axial bore 808 (e.g., 616 in FIG. 6) for rotatably receiving a pin or bolt (not shown), which can then be operably coupled to the support frame (e.g., or rotating gantry), for example. A bushing (not shown) can be provided in the bore 808 of the attachment member 802. Alternatively, the inner layer 806 may be provided as a pin and received in bearings or other suitable mounts of the support frame (e.g., or rotating gantry), for example. In such an alternative, the inner layer 806 may be substantially solid, without a bore 808 passing through the center, for example.

The attachment member 802 further comprises a middle layer 804 comprised of a substantially non-rotating dampening material. By way of example and not limitation, the middle layer may be comprised of a fiberglass, vinyl, doped plastics, fiberglass concrete dipped in resin, and/or butyl rubber. In this way, vibrations in inner layer (e.g., transferred from the support frame) are not passed to the rotating gantry via the attachment member 802 and/or vice-versa. Rather, vibrations attempting to pass through the attachment member 802 are dampened by the non-rotating dampening material in the middle layer 804.

The example attachment member 802 also comprises an outer layer 810, which may be made of a substantially rigid material (e.g., such as steel). The outer layer 810 is configured to be coupled to the base roller truck. Alternatively, the inner layer 806 may be configured to be operably coupled to the base roller truck and the outer layer 810 may be configured to be operably coupled to the base roller truck, for example.

It will be appreciated that while the example environment illustrates the non-rotating dampening material in an attachment member 802 of the roller truck, in another embodiment, a similar concept may be applied to the roller axles of the roller truck. For example, respective roller axles may be comprised of three or more layers, with at least one layer comprising a non-rotating dampening material. In such an embodiment, the rollers may be operably coupled to bolts or pins, for example, that are configured to be received in the axial bore, for example. Moreover, in such an embodiment, the outer layer may be configured to be coupled to the base roller truck. In this way, vibrations that transfer to the rollers from the rotating gantry are dampened (e.g., mitigating the possibility of the vibrations traversing the rest of the roller truck and being transferred to the support frame), for example.

Figure 9:
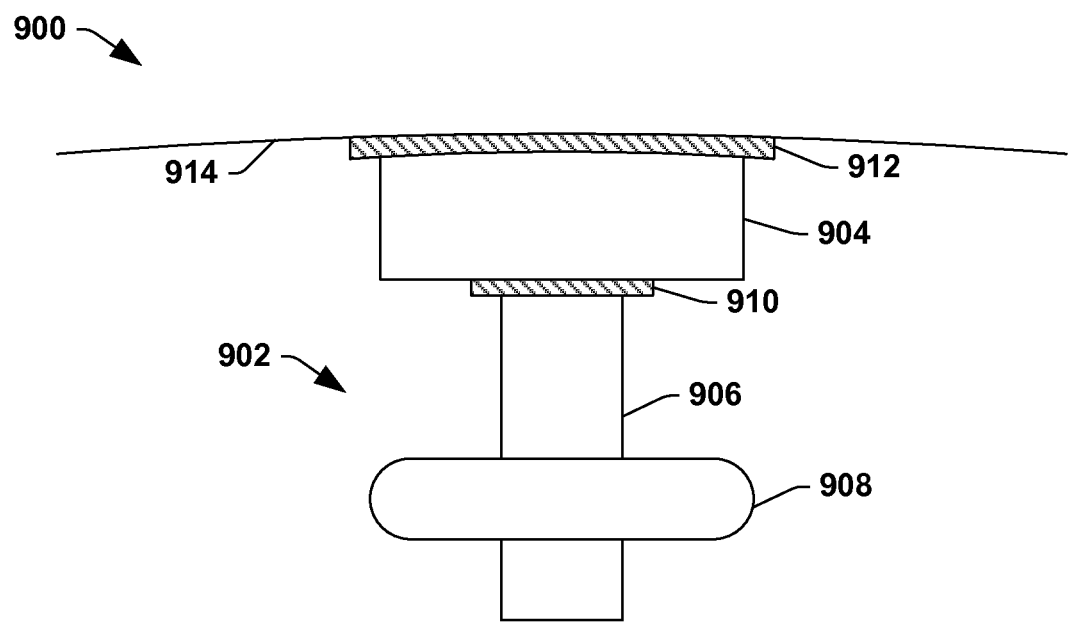
FIG. 9 illustrates an example z-axis roller truck comprising regions of non-rotating dampening material.

FIG. 9 illustrates an example environment 900 of a z-axis roller truck 902 (e.g., 206 in FIG. 2) that comprises a non-rotating dampening material. Specifically, the example z-axis roller truck comprises a shaft, or roller axle, upon which one or more rollers 908 are inserted, two non-rotating dampening material regions 910 and 912, and a base 904. It will be appreciated that while two non-rotating dampening material regions 910 and 912 are illustrated, another embodiment of the z-axis roller truck 902 may comprise merely one (e.g., or multiple) non-rotating dampening material region. That is, the z-axis roller truck 902 illustrated in the example environment 900 is merely intended to illustrate some of the many locations on a z-axis roller truck 902 whereon non-rotating dampening material may be inserted. It will be appreciated to those skilled in the art that the example embodiment is not intended to limit the possible locations on the z-axis roller truck 902 whereon non-rotating dampening material can be inserted. For example, in another embodiment, a shaft 906 supporting the roller 908 may be at least partially comprised of a non-rotating dampening material.

The z-axis roller truck 902 is configured to support a rotating gantry (e.g., 204 in FIG. 2). More particularly, the z-axis roller truck 902 is generally configured to mitigate movement of the rotating gantry in the z-dimension. In this way, the rotating gantry substantially remains in a same rotational plane during the examination. To do this, the z-axis roller truck 902 comprises one or more rollers 908 that rotate with the rotating gantry and mitigate the movement of the rotating gantry in the z-dimension (e.g., keeping it from tilting out of the page or into the page in FIG. 2). That is, the one or more rollers 908 are disposed in rolling contact with a side edge the rotating gantry. It will be appreciated that such rollers generally impose no substantial constraint on the rotation of the rotating gantry within the scanning plane so that scans can be accomplished and/or on the motion of the rotating gantry normal to a rotational axis so as to accommodate thermal expansion and contraction of the rotating gantry.

The one or more rollers 908 are coupled to the shaft 906, which is operably coupled to a base 904, and the base 904 is in return operably coupled to a support frame 914 (e.g., 210 in FIG. 2) (e.g., or the rotating gantry). Thus, the base 904 and the shaft 906 are typically substantially stationary while the roller(s) 908 rotates about the shaft 906, for example.

To dampen the vibrations, or vibration frequencies, dampening material may be inserted into the z-axis roller truck 902. For example, as illustrated herein, non-rotating dampening material may be inserted in a region 910 between the shaft 906 and the base 904 and/or may be inserted in a region 912 between the base 904 and the support frame 914, for example. As described above, the non-rotating dampening material may be sized (e.g., to a sufficient thickness), to mitigate the transfer of vibrations or vibration frequencies from the rotating gantry to the support frame 914 and may be operably coupled to the z-axis roller truck 902 and/or to the support frame 914 via a bonding material, such as an epoxy, for example.

In another embodiment, the shaft 906 of the z-axis roller truck 902 may be configured similar to the attachment member 802 illustrated in FIG. 8, and the z-axis roller truck 900 may or may not comprise non-rotating dampening regions 910, 912 as herein described. For example, the roller 908 may operably coupled to an inner layer (e.g. 806 in FIG. 8) of the shaft 906 via a pin or bolt and the shaft 906 may be operably coupled to the base 904 via an outer layer (e.g., 810 in FIG. 8). Alternative, the roller 908 may be operably coupled to the outer layer of the shaft 906 and the shaft may be operably coupled to the base 904 via a pin or bolt that is passed through a bore formed by the inner layer of the shaft 906, for example. A middle layer (e.g., 804 in FIG. 8) between the inner and outer layers may be comprised of a non-rotating dampening material, for example.

Figure 10:
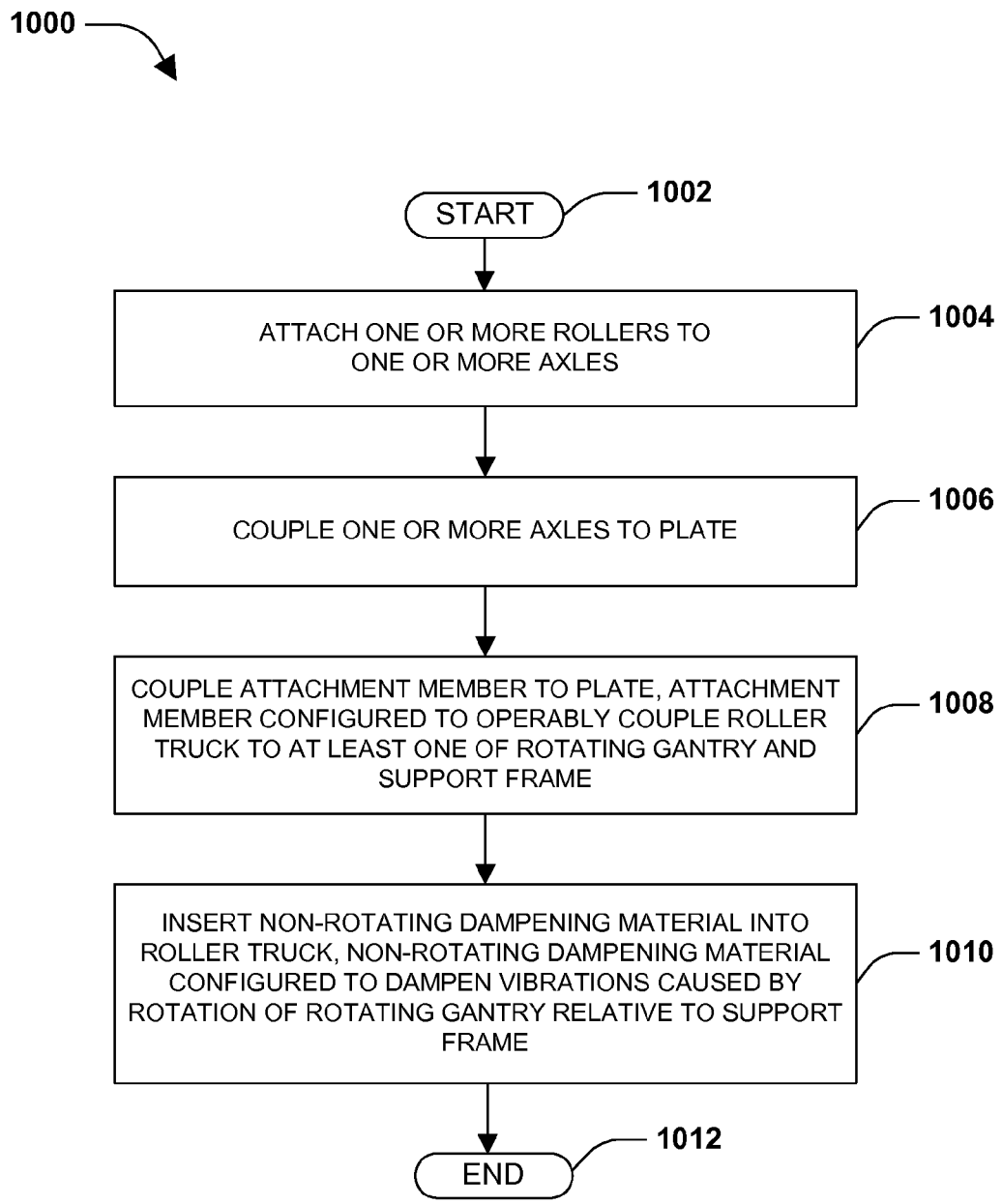
FIG. 10 is a flow diagram illustrating an example method for constructing a roller truck for supporting a rotating gantry and for allowing for rotation of the rotating gantry relative to a support frame.

FIG. 10 illustrates an example method 1000 for constructing a roller truck for supporting a rotating gantry and/or for allowing for rotation of the rotating gantry relative to a support frame. More particularly, the example method 1000 provides for constructing a roller truck comprising a non-rotating dampening material, such as the base roller trucks and/or the z-axis roller trucks described herein. It will be appreciated that such an example method finds particular application with the construction and/or use of roller trucks for a computed tomography (CT) scanner. However, the example method may also be used in other applications where dampening vibrations from a rotating structure may be useful.

The example method 1000 begins at 1002 and one or more rollers are attached to one or more roller axles at 1004. The roller(s), which may be made of a resilient material, such as such as rubber, nylon, or suitable a polymer, for example, is typically ground to a specified diameter and/or thickness and is configured to rest on at least one of the rotating gantry and/or the support frame. For example, in one embodiment, the roller(s) is configured to contact the rotating gantry and provide support for the rotating gantry (e.g., so that the rotating gantry remains in a rotational plane during the examination). It will be appreciated that such a roller(s) may further be configured to rotate along with the rotating gantry.

The one or more rollers may be attached to the one or more roller axles through bolts and/or pins, for example, and in one embodiment, at least one of the roller(s) and the roller axle(s) comprise bearings such that the roller(s) may rotate while the roller axle(s) is held substantially stationary. It will be appreciated that other configurations that allow the roller axle(s) to be held substantially stationary while the roller(s) rotates is also contemplated. Moreover, in one embodiment, one or more of the roller(s) and roller axle(s) are operably coupled together in a way that does not allow the roller(s) to rotate freely from the roller axle(s). Rather, in such an embodiment, one or more of the roller(s) and the roller axle(s) may rotate concurrently, for example.

Moreover, as described above, respective rollers may be operably coupled to a respective roller axle (e.g., such that no two rollers share a common roller axle) or two or more rollers may be coupled to a single roller axle. Thus, in one embodiment, such as illustrated in FIGS. 3-4, a plurality of rollers may be coupled to a single roller axle, or alternatively, merely one roller may be coupled to respective roller axles.

At 1006 in the example method 1000, the one or more roller axles are coupled to a plate. For example, as described with respect to FIG. 3, the plate may make up a sidewall structure of the roller truck, and the one or more roller axles may be operably coupled to the sidewall structure of the roller truck (e.g., using pins, bolts, epoxies, and/or other fastening items, techniques, etc. known to those skilled in the art). Alternatively, as described with respect to FIG. 6, the plate may makeup of a relatively flat (e.g., or curved) structure that is configured to provide rigidity to the roller truck and give the roller truck some structural form, and the one or more roller axles may be operably coupled to the structure (e.g., using pins, bolts, epoxies, and/or other fastening items, techniques, etc. known to those skilled in the art).

It will be appreciated that where the roller axle(s) is configured to rotate with the roller(s), the plate may comprise bearings and/or one or more other items, mechanisms, etc. that facilitate or allow the roller axle(s) to rotate substantially freely while the plate is held substantially stationary. Alternative, a portion of the roller axle(s) that is coupled to the plate may comprise such bearings, for example.

At 1008, an attachment member is coupled to the plate. The attachment member is configured to operably couple the roller truck to at least one of the rotating gantry and the support frame. For example, in one embodiment, one or more roller trucks are operably coupled to the rotating gantry and the roller(s) of the one or more roller trucks make contact with the support frame and rotate about the support frame as the rotating gantry rotates. In another embodiment, the rollers trucks are operably coupled to the support frame and the roller(s) of one or more roller trucks make contact with the rotating gantry. In such an embodiment, the roller trucks are generally substantially stationary relative to the support frame while the rotating gantry rotates, for example.

The attachment member, which may be configured to pivot as described above, may be operably coupled to the support frame and/or to the rotating gantry via a pin, bolt, or other fastening mechanism known to those skilled in the art.

In one example, where the roller truck comprises at least two roller axles, it is preferable that the attachment member is operably coupled to the plate between the two roller axles (e.g., preferably centered between the two roller axles); however, such a configuration is not necessarily required. Moreover, where the attachment member is configured to pivot, it will be appreciated that the attachment member and/or the support frame/rotating gantry to which the attachment member is operably coupled, may comprise bearings and/or one or more other items, mechanisms, etc. that facilitate or allow the attachment member to pivot, for example, as described above.

At 1010 in the example method, non-rotating dampening material is inserted into the roller truck. The non-rotating dampening material is configured to dampen vibrations caused by the rotation of the rotating gantry relative to the support frame. For example, in a CT application, the non-rotating dampening material may be configured to dampen a natural resonance to mitigate distortions in reconstructed images produced by the CT scanner.

As described above, the non-rotating dampening material may be comprised of any material known to those skilled in the art that dampens and/or deadens vibration frequencies. For example, fiberglass, vinyl, doped plastics, fiberglass concrete dipped in resin and/or butyl rubber may be considered for use as non-rotating dampening materials. It will be appreciated that the size (e.g., thickness) and/or location of the non-rotating dampening material may depend upon the type of non-rotating dampening material used and/or the vibration frequencies that are required to be dampened. For example, a thin layer of butyl rubber may dampen vibration frequencies to substantially the same and/or similar degree as a thicker layer of fiberglass. Thus, butyl rubber may be used in locations where a thin layer of non-rotating dampening material is preferred.

It will be appreciated that as described above, non-rotating dampening material may be inserted into numerous locations in the roller truck. Moreover, where the non-rotating dampening material is inserted may depend upon the type of roller truck the non-rotating dampening material is inserted into. By way of example and not limitation, in a z-axis roller truck (e.g., as described in FIGS. 2 and 9), the non-rotating dampening material may be inserted into the roller axle (e.g., which is sometimes referred to herein as a shaft 906 as illustrated in FIG. 9) and/or in regions where the roller axle makes contact with a base (e.g., 910 in FIG. 9) and/or in regions where a base of the z-axis roller truck makes contact with the support frame and/or rotating gantry (e.g., 912 in FIG. 9) (e.g., depending upon whether the z-axis roller truck(s) is operably coupled to the support frame or the rotating gantry).

In a base roller truck (e.g. as described in FIGS. 2-7), further locations for the insertion of non-rotating dampening material are contemplated. For example, as illustrated in FIGS. 3-5, non-rotating dampening material may be inserted into and/or coupled to a surface of a plate to which the roller axles and/or the attachment member are operably coupled. For example, recesses and/or grooves may be cut in the plate and non-rotating dampening material may be inserted therein. Additionally or alternatively, the attachment member and/or the roller axles themselves may comprise the non-rotating dampening material and/or the non-rotating dampening material may be inserted between the attachment member and the plate and/or between the roller axle(s) and the plate, for example (e.g., as illustrated in FIGS. 7 and 8). In yet another embodiment, the plate itself may be comprised of a plurality of layers, at least one layer of which is a non-rotating dampening material. For example, as illustrated in FIG. 6, the plate may be comprised of three layers, with a middle layer (e.g., sandwiched between the other two layers) comprising the non-rotating dampening material (e.g., such that the non-rotating dampening material is inserted into the plate itself).

It will be appreciated that while numerous example locations for the insertion of non-rotating dampening material is described herein, the scope of the disclosure is not intended to be limited to such examples. That is, to the extent practicable, non-rotating dampening material may be inserted virtually at any location in the roller truck where it would be able to dampen or mitigate the transmission of vibration frequencies from the rotating gantry to the support frame and/or vice-versa. Moreover, it will be appreciated that non-rotating dampening material can be inserted into any and/or all of the one or more locations herein described. Thus, non-rotating dampening material may be comprised merely within a single region of a roller truck or may be comprised within a plurality of regions. Additionally, it will be appreciated that different roller trucks may comprise different amounts of non-rotating dampening material. For example, a first base roller truck may comprise substantially zero non-rotating dampening material while another base roller truck may comprise one or more regions of non-rotating dampening material. Similarly, different types of roller trucks may comprise different amounts of non-rotating dampening material. For example, one or more z-axis roller trucks may comprise a minimal amount of (e.g., if any) non-rotating dampening material while one or more base roller trucks and/or other z-axis roller trucks comprise a more substantial amount of non-rotating dampening material. In another example, one or more z-axis roller trucks may comprise more non-rotating dampening material than one or more base roller trucks. Thus, the location and/or amount of non-rotating dampening material may depend upon such things as the ease of inserting the material into the roller truck, design modifications required to insert the material into the roller truck, and/or the application for the roller truck, for example.

At 1012, the example method 1000 ends.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An apparatus comprising:
   a support frame;
   a rotating gantry configured for rotation relative to the support frame; and
   a roller truck configured to at least partially support the rotating gantry and facilitate rotation of the rotating gantry relative to the support frame, the roller truck comprising:
      a plate comprising:
         a first layer defining a first surface;
         a second layer comprising a non-rotating dampening material for dampening vibrations caused by the rotation of the rotating gantry; and
         a third layer defining a second surface, the second layer situated between the first layer and the third layer;
      at least one roller axle operably coupled to the first surface;
      an attachment member operably coupled to the second surface, the attachment member configured to operably couple the roller truck to at least one of the support frame or the rotating gantry; and
      one or more rollers rotatably mounted on the at least one roller axle and configured to at least partially support the rotating gantry and to facilitate rotation of the rotating gantry relative to the support frame, wherein the at least one roller axle is not operably coupled to a layer to which the attachment member is operably coupled.

2. The apparatus of claim 1, the rotating gantry comprising at least one of an x-ray source or a detector array.

3. The apparatus of claim 1, the non-rotating dampening material configured to dampen a natural resonance to mitigate distortions in reconstructed images produced by a CT scanner of the apparatus.

4. The apparatus of claim 1, the attachment member comprising:
   a first layer; and
   a second layer circumferentially surrounding the first layer and comprising a dampening material.

5. The apparatus of claim 1, the roller axle comprising:
   a first layer; and
   a second layer circumferentially surrounding the first layer and comprising a dampening material.

6. The apparatus of claim 1, comprising a dampening material disposed between the attachment member and the second surface of the plate.

7. The apparatus of claim 1, comprising a dampening material disposed between the roller axle and the first surface of the plate.

8. The apparatus of claim 1, the first layer comprising a metal.

9. The apparatus of claim 1, the third layer comprising a metal.

10. The apparatus of claim 1, the first layer and the third layer comprising metal and the second layer void of metal.

11. The apparatus of claim 1, the non-rotating dampening material comprising fiberglass.

12. The apparatus of claim 1, the non-rotating dampening material comprising vinyl.

13. The apparatus of claim 1, the non-rotating dampening material comprising fiberglass concrete dipped in resin.

14. The apparatus of claim 1, the non-rotating dampening material comprising butyl rubber.

15. A method for constructing a roller truck for supporting a rotating gantry and for allowing for rotation of the rotating gantry relative to a support frame, comprising:
   attaching one or more rollers to one or more roller axles;
   coupling the one or more roller axles to a plate;
   coupling an attachment member to the plate, the attachment member configured to operably couple the roller truck to at least one of the rotating gantry or the support frame; and
   inserting a non-rotating dampening material into at least one of:
      the one or more roller axles, or
      the attachment member, the non-rotating dampening material configured to dampen vibrations caused by the rotation of the rotating gantry relative to the support frame.

16. The method of claim 15, comprising inserting additional dampening material between at least one of:
   the one or more roller axles and the plate, or
   the attachment member and the plate.

17. The method of claim 15, comprising inserting additional dampening material into the plate.

18. The method of claim 15, the roller truck constructed for use on a computed tomography (CT) scanner.

19. A computed tomography (CT) apparatus comprising:
   a support frame;
   a rotating gantry configured for rotation relative to the support frame, the rotating gantry comprising an x-ray source and a detector array; and
   a roller truck configured to support the rotating gantry and to allow the rotating gantry to rotate relative to the support frame, the roller truck comprising:
      a plate comprising:
         a first layer defining a first surface;
         a second layer comprising a dampening material configured to dampen vibrations caused by the rotation of the rotating gantry relative to the support frame; and a third layer defining a second surface, the second layer situated between the first layer and the third layer;
at least one roller axle operably coupled to the first surface;
an attachment member operably coupled to the second surface, the attachment member configured to operably couple the roller truck to at least one of the support frame or the rotating gantry; and
one or more rollers rotatably mounted on the at least one roller axle and configured to at least partially support the rotating gantry and to facilitate rotation of the rotating gantry relative to the support frame, wherein the at least one roller axle is not operably coupled to a layer to which the attachment member is operably coupled.

20. The CT apparatus of claim 19, a material composition of the first layer different than a material composition of the second layer.

* * * * *